United States Patent [19]

Wilson

[11] Patent Number: 5,147,790
[45] Date of Patent: * Sep. 15, 1992

[54] SERUM-INDEPENDENT HUMAN CELL LINES, PROCESS FOR PRODUCING SAME, AND PROCESSES FOR PRODUCING PROTEINS THEREFROM

[75] Inventor: Elaine L. Wilson, Newlands, South Africa

[73] Assignee: t-PA Technology Trust

[*] Notice: The portion of the term of this patent subsequent to Jan. 17, 2006 has been disclaimed.

[21] Appl. No.: 253,190

[22] Filed: Oct. 4, 1988

Related U.S. Application Data

[63] Continuation of Ser. No. 854,729, Apr. 17, 1986, which is a continuation of Ser. No. 754,798, Jul. 12, 1985, abandoned, which is a continuation of Ser. No. 566,467, Dec. 28, 1983, abandoned.

[30] Foreign Application Priority Data

Dec. 30, 1982 [ZA] South Africa ................. 82/9576
Jun. 22, 1983 [ZA] South Africa ................. 83/4576

[51] Int. Cl.$^5$ .................. C12P 21/00; C12N 5/06
[52] U.S. Cl. .................. 435/70.3; 435/240.2; 435/240.21
[58] Field of Search ............ 435/240.2, 240.21, 240.3, 435/240.31, 70.3, 212, 226

[56] References Cited

FOREIGN PATENT DOCUMENTS 0041766 12/1981 European Pat. Off. ............ 435/240

OTHER PUBLICATIONS

Kaighn, M., "Growth Control of Prostatic Carcinoma Cells in Serum-Free Media: Interrelationship of Hormone Response, Cell Density and Nutricat Media", *Proceedings of the National Academy of Sciences,* 78; pp. 5673-5676, (1981).

*Primary Examiner*—Douglas W. Robinson
*Assistant Examiner*—Marian C. Knode
*Attorney, Agent, or Firm*—St. Onge Steward Johnston & Reens

[57] ABSTRACT

Human cell lines which proliferate in the absence of serum or of any macromolecular growth factors are produced by a three step procedure comprising removing serum containing culture medium from the culture of a human cell line which requires serum or macromolecular growth factors for growth, and replacing it with culture medium which is deprived of serum and of any macromolecular growth factors, feeding the adherent or non-adherent cells with serum and growth factor free culture medium using conventional cell culture conditions, culturing the cells until they propagate reproducibly and indefinitely in the absence of serum and of any macromolecular growth factors and a serum and growth factor independent cell line has been established. The novel cell lines can be used for the production of proteins, especially plasminogen activators.

8 Claims, No Drawings

025
SERUM-INDEPENDENT HUMAN CELL LINES, PROCESS FOR PRODUCING SAME, AND PROCESSES FOR PRODUCING PROTEINS THEREFROM

This is a continuation of co-pending application Ser. No. 06/854,729 filed on Apr. 17, 1986, now U.S. Pat. No. 4,798,796, which is a continuation of Ser. No. 06/754798 filed on Jul. 12, 1985, abandoned, which is a continuation of Ser. No. 06/566467 filed Dec. 28, 1983, abandoned.

FIELD OF THE INVENTION

The invention relates to human cell lines capable of proliferating in the absence of serum or of any exogenous macromolecular growth factor, to the use of such cell lines for the production of biologically active compounds, to biologically active compounds produced by said cell lines and to the use thereof in the treatment of human diseases. The invention also provides processes for the production of said cell lines and said biologically active compounds.

BACKGROUND OF THE INVENTION

With the advent of recombinant DNA technology and cell culture techniques in recent years, the controlled biological production of useful and pharmacologically interesting compounds, especially proteins, such as interferon, insulin and antigens, has become possible. There is an increasing need for the development of biological systems ensuring the large scale production of further proteins of biological, especially pharmacological, interest.

The term "protein" as used hereinbefore and hereinafter is intended to include polypeptides of high molecular weight, e.g. of over about 34000, and also polypeptides of lower molecular weight, e.g. of below about 34000, and derivatives thereof, such as glycosylated, phosphated and sulfated derivatives.

The advances in recombinant DNA technology make it feasible to introduce the gene encoding a desired protein into microorganisms and then induce the microorganisms to synthesize the protein. However, many biologically important molecules cannot be synthesized by this technology. This is especially true for those molecules the structure of which is not yet known. In most cases, the proteins secreted by genetically modified microorganisms are not a faithful replica of the authentic molecules but differ from the latter with respect to the N and C termini of the amino acid sequence. This fact is due to the experimental procedure in recombinant DNA technology. Furthermore, glycosylated proteins cannot be produced by microorganisms, such as bacteria and to a certain extent also yeast, which lack the necessary cellular machinery. In many cases, cell and tissue culture technique can be advantageously made use of. As cell cultures originate from intact organisms the proteins produced by the cell cultures correspond to the naturally occuring proteins in all respects.

However, cultivation of cells of higher organisms, such as mammalian cells, on a large scale is a difficult problem. The nutrient requirements of such cells are more stringent than those of most microorganisms which proliferate in artificial media. The growth medium of most mammalian cells described so far has to include serum which is very expensive. The cost of serum largely determines the economic feasibility of the cell culture technique and may limit its applicability to the production of proteins which are not available otherwise. Some cells can be cultured in serum-free medium supplemented with hormones or growth factors such as transferrin, insulin, epidermal, fibroblast or nerve growth factor. In most cases, however, cells will not multiply indefinitely in these serum-free media.

Cell lines proliferating in a serum-free medium are of particular importance for the production of such proteins which are susceptible to destruction or contamination by serum or exogenously added growth factors. Such protein is for example pro-tissue plasminogen activator (pro-TPA).

The so-called plasminogen activators, have become the subject of scientific investigations showing their evident clinical applicability in the lysis of blood clots. Blood clots are composed of fibrin which has been formed from its soluble precursor fibrinogen under the action of the enzyme thrombin. They are one of the major causes of morbidity and of mortality in humans and dissolving them without side effects is difficult to achieve.

Mammalian plasma contains an enzymatic system capable of dissolving the fibrin in blood clots. One component of the fibrinolytic system consists of the enzymes, plasminogen activators, which convert plasminogen (an inactive proenzyme form of plasmin) into the proteolytic enzyme plasmin. Plasmin then degrades the fibrin network of the clots to form soluble products. In cases where the thrombolytic potential of the body is insufficient to remove intravascular thrombi formed, for example in patients suffering from thromboembolisms or post-surgical complications, it may be indispensable to use exogenously administered thrombolytic agents.

There are two activators of human plasminogen which are commerically available for thrombolytic therapy: urokinase, a serine protease isolated from human urine or cultured kidney cells, and streptokinase, a bacterial protein obtainable from streptococci. Since neither enzyme has a specific affinity for fibrin, thrombolysis with these substances is associated with systemic activation of plasminogen which can produce indiscriminate digestion of coagulation proteins, and significantly increase the risk of internal bleeding (hemorrhage) during treatment. Another disadvantage of urokinase is its very short useful half-life following its injection into humans. For this reason, high doses of urokinase are needed to achieve effective fibrinolysis. Streptokinase being a protein foreign to man, gives rise to the production of neutralizing antibodies which block its action, and to allergic reactions which are harmful and potentially fatal.

Another group of plasminogen activators, called tissue plasminogen activators (hereinafter referred to as "TPAs") are known to exist in most human tissues. TPAs originating from different tissues possibly differ from each other with respect to their molecular properties but are immunologically similar. They differ from urokinase with respect to their chemical and immunological properties, in their greatly enhanced fibrinolytic action in the presence of fibrin, as well as in their high affinity for fibrin [cf. S. Thorsen et al., Thromb. Diath. Haemorrh. 28, 65–74 (1972), D. C. Rijken and D. Collen, J. Biol. Chem. 256, 7035–7041 (1981)]. Because of their high affinity for fibrin, the action of TPAs is confined to the locality of the clot thereby reducing significantly the danger of uncontrolled hemorrhage.

The following scheme shows the relationship between plasminogen, plasmin, fibrin and the various plasminogen activators.

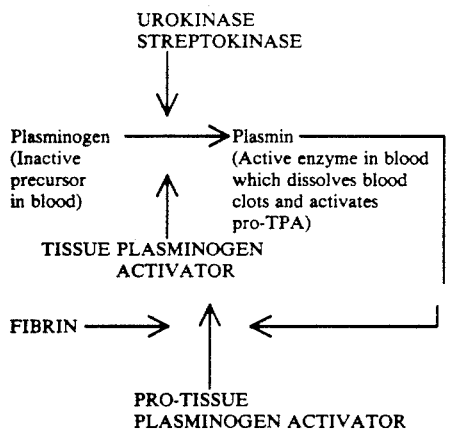

Recently, two patients suffering from coagulation disorders have been successfully treated with a TPA isolated from the culture fluid of a human melanoma cell line [cf. W. Weimar et al., *The Lancet* (1981), 1018-1020]. There are two molecular forms of TPA: the active two-chain form and an inactive one-chain form [precursor TPA or "pro-TPA"; for reference, cf. D. C. Rijken and D. Collen, loc. cit.; D. C. Rijken et al., *J. Biol. Chem.* 257, 2920-2925 (1982) and P. Wallén et al. *Progr. Fibrin.* 5, 16-23 (1982)]. Pro-TPA can be converted to active TPA by incubation with fibrin or by the influence of plasmin which by this cascade-like reaction triggers its own synthesis.

Sources of human TPA include extracts of various human tissues (which are not available for commercial exploitation) and various human tumor cells which have been shown to release TPAs to a varying extent [E. L. Wilson et al., *Cancer Research* 40, 933-938 (1980); E. L. Wilson et al., *Blood* 61, 568-574 (1983)].

In a recently filed patent application (EP 41766, inventors D. Collen, D. C. Rijken and O. Matsuo) a TPA with a molecular weight of 72000 is disclosed which has been isolated from a cultured human melanoma cell line (Bowes) and which is probably identical to the TPA already described by E. L. Wilson et al. [*Cancer Research* 40, 933-938 (1980)]. Like other cell lines known so far, this human melanoma cell line, Bowes, requires the presence of serum for growth, e.g. foetal calf serum. However, serum is very expensive and contains proteinaceous components which contaminate the produced TPA and prevent the isolation of high amounts of pro-TPA. This may lead to a tedious and laborious purification procedure for either TPA or pro-TPA.

OBJECT OF THE INVENTION

The present invention overcomes the disadvantages of the hitherto known cell lines and makes it possible to produce new human cell lines which grow in the absence of serum or of any exogenous macromolecular growth factor. It is also an object of the present invention to provide new pharmacologically active proteins, such as human tissue plasminogen activator and especially pro-activator, secreted by such a serum-independent cell line.

DETAILED DESCRIPTION OF THE INVENTION

Production of serum-independent human cell lines

The present invention provides new human cell lines which grow in the absence of serum or of any exogenous macromolecular growth factor, such as insulin, transferrin, epidermal growth factor etc. The cells according to the invention are capable of adhering to the culture vessel even in the absence of serum or fibronectin. The major advantages of the new cell lines are:

(1) an enormous reduction in costs as serum, such as foetal calf serum, is very expensive, (2) the very cheap and simple purification of products produced by the new cell lines as there are no serum contaminants in the medium and the product can easily be purified from the serum-free medium, and (3) the possibility of producing proteins which, due to the presence of proteases in serum, cannot be obtained (or which can only be obtained in poor yields) from serum-dependent cell lines.

The process for the production of the new serum-independent human cell lines comprises the steps of:

a. removing serum containing medium from the culture of a serum-dependent human cell line and replacing it with serum-free medium, b. feeding the adherent or not adherent cells with serum-free medium, and c. allowing the cells to grow until a serum-independent cell line has been established.

The term "serum-free medium" as used hereinbefore and hereinafter is intended to designate a medium which is not only deprived of serum but also of any macromolecular growth factor. Accordingly, a cell line which grows in the absence of both serum and exogenous macromolecular growth factors is referred to as a "serum-independent cell line".

The serum-dependent human cell line used as "starting material" in the above process is especially a continuous one and may originate from human neoplasms, such as melanoma, malignant teratoma, sarcoma, glioblastoma, meningioma, neuroblastoma, lipoma, adenoma, carcinoma of breast or carcinoma of the bladder. Preferred cell lines are those which produce TPA and/or pro-TPA. In a preferred embodiment of the present invention, a human melanoma cell line, especially the Bowes melanoma cell line (hereinafter referred to as "Bowes I" cell line) is used. Cell lines derived from normal human tissue can also be used as "starting material", although they have a limited in vitro life span (the growing stops usually after about, for example, 50 cell divisions), but are less important with respect to the present invention.

The serum-free nutrient medium is, for example, a commercially available medium, such as minimal Eagle's medium (MEM), MEM-Spinners medium, Dulbecco's modified Eagle's medium (DMEM) or Roswell Park Memorial Institute culture medium (RPMI)-1640. Other equivalent media may be used as well. The serum-free medium may contain a sufficient quantity of a buffering agent, such as sodium hydrogencarbonate, to maintain a stable pH. As cells in culture are deprived of the elaborate immune defense system that is an integral part of the intact organism, antibiotics, such as penicillin, streptomycin, tylocine and the like, are advantageously included to prevent infection of the culture.

Normal human cells will ordinarily grow only if attached to the surface, whereas tumor cells often more readily grow in suspension. Laboratory vessels for anchorage dependent cells are well known to the art. They range from "microwell" plates and flat-bottomed Petri dishes through tissue flasks of various sizes or cylindrical bottles, named roller bottles, which rotate continuously. Anchorage independent cells may be grown in cultivation vessels which are mechanically agitated or where a homogeneous suspension is maintained by mixing with a gas stream.

For example, the process of the present invention may be carried out in a tissue culture flask containing a confluent or nearly confluent mono-layer of a human cell line, for example a human melanoma cell line, especially melanoma Bowes I, which has grown in a serum containing nutrient medium. The further procedure is performed in a humid atmosphere containing carbon dioxide, for example in a humid atmosphere of approximately 95% air and approximately 5% $CO_2$, at a temperature of between about 35° C. and about 40° C., especially at approximately 37° C. The serum containing medium is discarded and replaced by a serum-free medium, for example RPMI-1640 or DMEM. After a few days cells start to detach from the surface of the flask and float free in the medium. After a few weeks the majority of the cells will have died in a medium deprived of serum or any growth factors. To maintain cell viability conditioned medium is added to the cultures during the period of adaptation to serum-free medium. Conditioned medium may be collected from a companion cell culture, kept for a time period of, for example, 24 hours in serum-free medium. Serum-free medium containing conditioned medium has to be changed at intervals of, for example, 3 to 7 days until the cell number has sufficiently increased, i.e., until approximately one third of the vessel surface is covered. At this stage, the conditioned medium is no longer required and the cells are fed with serum-free medium alone. When a confluent monolayer has formed, the cells have to be passaged, for example by vigorous tapping of the vessel whereby most of the cells are dislodged from the surface, or with the aid of ethylene-diaminetetraacetic acid (EDTA), taking care that reseeding of fresh culture flasks is performed at a sufficiently high cell density in order to ensure survival. Growing and passaging the cells at confluence is continued until the cells grow as stable and adherent monolayers. In this manner, over a period of, for example, 1 to 6 months, especially 1 to 3 months, a serum-independent cell line is established.

In an alternative approach the serum-independent cell line can be established without adding conditioned medium collected from the companion serum-dependent cell culture, provided that the cell density is high enough. In this case the cells condition their own medium. The cell density can be kept high by not discarding the non-adherent cells. For example, after a few days in serum-free medium the majority of the cells detach from the tissue culture vessel and float free in the medium as described above. The cells which detach remain viable as long as they are kept at a sufficiently high density. If the serum-free medium containing the non adherent but viable cells is centrifuged and the cell pellet taken up in fresh serum-free medium and added back to the flask containing the sparse adherent cells, the adherent cells will start to grow. In this case the cells in suspension together with the adherent cells are conditioning their own medium.

Another method of preparing the "conditioned medium" in the presence of the adherent cells consists in replacing part of the serum-free medium, approximately half thereof, by fresh serum-free medium and repeating this process every 24 to 72 hours until a high enough cell density is obtained (after about 3 weeks). The cells may then be passaged, e.g. with the aid of EDTA. At the first passage the fresh serum-free medium is supplemented to about 40% of the conditioned medium removed from the culture prior to EDTA-treatment, whereafter the cells will continue to divide in the absence of conditioned medium. The cell density should be sufficiently high, which is at about 30% or more, preferably at about 60–70% confluency.

At a low cell density, i.e. at about 20% confluency or at about $1 \times 10^5$ cells/ml in the case of suspension cultures, the cells need conditioned medium for growth. At a high cell density, i.e. at about 60 to about 70% confluency or at about $2 \times 10^5$ to $5 \times 10^5$ or more cells/ml in the case of suspension cultures, the cells will grow and proliferate in serum-free medium without the addition of conditioned medium.

The serum-independent cell lines can be grown as adherent cultures, for example at the inner wall of a laboratory vessel, or as suspension cultures.

The invention also extends to new human lines, especially human melanoma cell lines, capable of proliferating in a serum-free culture medium, especially when prepared according to the process of the present invention.

The invention relates also to mutant cell lines obtainable from the cell lines according to the present invention and capable of proliferating in a serum-free culture medium. Mutants are formed spontaneously or can be produced in a manner known per se. For example, mutants may be obtained by chemical means, e.g. by the action of a mutagen, such as N-methyl-N'-nitro-N-nitrosoguanidine or mustard oils, or by irradiation, e.g. with ultraviolet rays or X-rays.

Preferred serum-independent cell lines and mutant cell lines according to the present invention are those which produce TPA and/or pro-TPA.

The new human cell lines and the mutant cell lines obtainable therefrom according to the present invention, have an unlimited life span and can be used in a similar manner as the original serum-dependent cell lines, for example for the commercial production of biologically active compounds, such as proteins, for example interferons, antigens, angiogenic factors and especially plasminogen activators, under serum-free conditions or for the manufacture of hybridoma cell lines.

As stated above, the melanoma cell line Bowes I known to secrete high levels of tissue plasminogen activator (cf. EP 41766) is preferably used as "starting material" for the process according to the invention. The resulting serum-independent new cell line, hereinafter referred to as "Bowes II", especially a substantially pure culture thereof, and the process for the preparation thereof are also subjects of the present invention.

The invention concerns also serum-independent mutant cell lines obtainable from the Bowes II cell line and capable of secreting tissue plasminogen activator, and the process for the preparation thereof.

The new serum-independent cell lines differ from the corresponding parent cell lines which are serum dependent, in many respects. For example, Bowes II cells differ from the parent Bowes I melanoma cells in their morphological appearance. When examined under phase contrast microscopy, it becomes evident that mitoses are noticeably more frequent in Bowes II cells than in Bowes I cells which have been serum deprived. Addition of serum to Bowes II cells produces a marked morphological change.

The preferred serum-independent cell lines according to the invention, especially the Bowes II cell line, secrete high levels of tissue plasminogen activator which, in contrast to the parent serum-dependent cell lines, such as the Bowes I cell line, is predominantly in the pro-activator form. Apart from TPA and pro-TPA the new cell lines produce further pharmacologically valuable substances. For example, the Bowes II cell line produces its own growth factor and a tumor necrotic factor. These proteins and their preparation as well as the harvest fluids obtainable from the new serum-independent cell lines, especially the Bowes II cell line, are also subjects of the present invention.

Cultivation of serum-independent human cells and harvest of culture fluids

Serum independent human cells may be grown essentially as described above. For example, Bowes II cells are seeded into tissue culture flasks at a sufficient cell density to ensure survival and are allowed to grow in a serum-free medium, for example RPMI-1640, supplemented with antibiotics, at a temperature of between about 35° C. and about 40° C. especially at approximately 37° C. in a humid atmosphere of air containing approximately 5% $CO_2$. The taking of harvest fluids may be started as soon as the cells become adherent and may be repeated, for example, at 24 hour intervals. Daily collection of harvest fluids can be continued until confluence of the monolayers necessitates passaging to fresh culture vessels.

As the proliferation rate of Bowes II cells cultured in serum-free medium is very low (the doubling time amounts to 6 days; compared to a doubling time of approximately 1 day of the parent Bowes I melanoma cells) passaging is required only infrequently (at intervals of approximately 4–6 weeks) and the harvest fluids can be collected from one flask for a period of approximately 3–6 months, thus saving considerable time and effort and making the collection of the fluids a simple task. It is also possible to enhance occasionally the proliferation rate of Bowes II cells by adding a growth factor, e.g. insulin, to the culture medium.

Petri dishes, tissue culture flasks and other vessels useful in laboratory work cannot provide a large enough ratio of surface area to volume for practical large-scale culture of serum-independent cells attached to the surface. For large-scale production the area-to-volume ratio may be increased by various means known to the art. For example, cells can be grown on spongy polymers, on stacks of thin plates, on small beads and the like.

Alternatively, the new serum-independent cell lines, such as Bowes II, can be grown in suspension. Large-scale fermenters which are suitable for cultivation in suspension, are well known to the art and have been developed by modifying the fermenters for single-celled microorganisms. In order to keep the cells uniformly suspended in the medium and to distribute dissolved gases (e.g. oxygen) evenly, agitation is required. This can be done by means of conventional turbine agitators, marine propeller shaped agitators, vibromixers which oscillate vertically, and the like. Slow agitation is preferred in order to prevent the cells from being damaged. Homogeneous agitation can also be maintained by passing a gas stream through the culture.

Harvest fluids obtained from serum independent human cells, such as Bowes II cells, will have to be centrifuged to remove detached cells and cell debris. It is advisable to add a nonionic detergent to the medium to prevent the adsorption of TPA, pro-TPA and other valuable substances secreted by the cells, to the vessel surface and to preserve enzyme activity. Preferably, the nonionic detergent, such as Triton X-100 ® or Tween 80 ®, is added to a final concentration of approximately 0.01–0.1%. As highest activity is maintained at pH 5.5–6.0, the harvest fluids are acidified with a weak acid, such as a lower alkanoic acid, e.g. with acetic acid, to this pH before storage at low temperature, for example at approximately 4° C. for 48 hours or, for a prolonged time, at −20° C.

The content of TPA, pro-TPA and other valuable substances in the harvest fluids may be determined by means of conventional techniques. For example, the TPA content may be measured by the $^{125}$I-fibrin assay or by a fluorometric assay. In the first, there is measured the time course of plasminogen dependent release of radioactive fibrin-degradation peptides from $^{125}$I-labelled fibrin deposited as an insoluble coating on the surface of plastic wells [cf. E. L. Wilson and E. Dowdle, *Int. J. Cancer* 22, 390–399 (1978)]. In the second, the increase in fluorescence that results from the amidolysis of an appropriate synthetic substrate, such as Cbz-Gly-Gly-Arg-AMC (AMC: aminomethyl coumarin residue) or Boc-Val-Gly-Arg-AMC, is measured [cf. M. Zimmerman et al., *Proc. Natl. Acad. Sci.* U.S.A. 75, 750–753 (1978)]. Whereas the $^{125}$I-fibrin assay gives the total enzyme activity of both TPA and pro-TPA, the fluorimetric assay can be conducted in such a manner that merely TPA activity is determined or, alternatively, after treating the harvest fluid with plasmin which converts pro-TPA to TPA, that both TPA and pro-TPA are included.

Using the above TPA assays, it can be shown that the harvest fluids obtainable according to the present invention contain pro-TPA at a high percentage. This is probably due to the fact that the culture medium used lacks plasmin or other proteases which may convert pro-TPA to TPA. The predominance of pro-TPA in harvest fluids obtained from, for example, cultured Bowes II cells contrasts strikingly with harvest fluids obtained from Bowes I melanoma cells which contain pro-TPA to a minor extent.

Isolation and purification of proteins secreted by serum independent cells

Isolation of the desired proteins from the culture fluid obtained from serum-independent cells, such as Bowes II cells, and their purification may be effected in principle in any suitable way which is common in protein chemistry, such as by fractionated precipitation with, for example, inorganic salts, gel filtration, for example, on cross-linked dextrans or agarose, gel electrophoresis or chromatographic means, such as, for instance, adsorption chromatography, ion exchange chromatography or affinity chromatography. For the isolation and purification of TPA and pro-TPA, such methods include, for example, the following:

Chromatography on zinc-chelate-agarose, concanavalin A-agarose and Sephadex G-150 ® [cf. D. C. Rijken and D. Collen, *J. Biol. Chem.* 256, 7035–7041 (1981)]. The harvest fluid is passed through a zinc-chelate-agarose column. The adsorbed enzyme is eluted with an imidazole containing buffer. The obtained solution is applied to a concanavalin A-agarose column. Elution can be performed with methylmannoside and KSCN. In the last step, the enzyme is gel-filtered on a Sephadex G-150 ® column.

Chromatography on Affi-Gel Blue ® and aminobenzamidine-Sepharose ® [cf. L. C. Gilbert and J. T. Wachsman, *Biochim. Biophys. Acta*, 704, 450–460 (1982)]. The enzyme is successively adsorbed to Affi-Gel Blue ® and aminobenzamidine-Sepharose ®. Desorption can be performed with a buffer containing arginine.

Selective adsorption of TPA and pro-TPA on a support of specific affinity of soluble fibrin fragments which are covalently fixed on an insoluble matrix, e.g. dextran [cf. European Patent No. 23 860]. The adsorbed enzyme may be eluted with an acetic acid buffer of pH 4.2.

Chromatography on an immunoaffinity column of anti-TPA antibodies, especially monoclonal anti-TPA antibodies, bound to an insoluble matrix, such as Affi-Gel ® or Sephadex-4B ®.

Affinity chromatography on DE-3 Sepharose ®. The seeds of the legume *Erythrina latissima* contain a trypsin inhibitor called DE-3 [F. J. Joubert et al., *Hoppe-Seyler's Zeitschr. Physiol. Chem.* 302, 531–538 (1981)]. It has been found that DE-3 is also able to inhibit TPA actively. Thus, the purified DE-3 inhibitor may be coupled to an insoluble matrix using standard procedures. The medium containing TPA and pro-TPA will adsorb and can be eluted by a buffer containing a chaotropic agent, e.g. KSCN.

Electrophoresis on polyacrylamide gels containing SDS (SDS-PAGE). This method is especially used for analytical purposes and for the determination of molecular weights.

In order to obtain a sufficiently pure product, a single procedure or some consecutive purification steps may be chosen. Furthermore, additional purification steps, for example dialysis in an appropriate buffer mixture, reverse phase HPLC and the like, may be necessary.

For example, the harvest fluids may be subjected to chromatography on zinc-chelate-agarose, concanavalin A-agarose and Sephadex G-150 ® as a first isolation step (which may also serve to concentrate the desired protein present in the large volumes of harvest fluid) and the enriched protein obtained may finally be purified by affinity chromatography.

In a preferred embodiment of the present invention, the harvest fluid obtained from serum-independent human cells, such as Bowes II cells, containing TPA and pro-TPA is centrifuged to remove whole cells and cellular debris and is then passed at room temperature through a column consisting of an insoluble matrix to which an affinity reagent selective for TPA and pro-TPA has been coupled, for example BrCN activated Sepharose ® to which the DE-3 inhibitor has been coupled. After washing the column, the adsorbed TPA and pro-TPA is desorbed by treating the column with a buffer solution, for example phosphate buffered saline, having a pH of approximately 5.5–6.0 and containing a chaotropic agent, such as KSCN, from about 1.4 to about 2.0 molar, preferably 1.6 molar. Alternatively, benzamidine or arginine may be chosen as desorbing agent.

In an alternative approach, TPA and pro-TPA are isolated by means of chromatography on a monoclonal antibody column which has been prepared by coupling of monoclonal anti-TPA antibodies to, for example, Affi-Gel ®.

Advantageously, a detergent, especially a nonionic detergent, such as Triton X-100 ® or Tween 80 ®, is added to all buffer solutions used in the purification steps, in order to prevent the adsorption of TPA and pro-TPA to the vessel surfaces and to improve stability. The detergent may be added to a final concentration of 0.01–0.1%.

The resulting purified solution contains TPA and pro-TPA. For the preparation of TPA which is free of any pro-TPA, the pro-TPA is enzymatically converted into TPA, for example by the action of plasmin or an enzyme having an equivalent effect on pro-TPA.

In a preferred embodiment of the present invention, pro-TPA is isolated in substantially pure form, free of TPA. Pro-TPA is a true pro-enzyme, i.e. it is the enzymatically inactive form of TPA. Pro-TPA adsorbs to fibrin to a greater extent than TPA and it is therefore more selective than TPA in bringing about fibrinolysis, because it first attaches to fibrin and is only then converted into TPA whereas with TPA there exists a limited possibility that it will activate some plasminogen in the blood stream rather than at the fibrin site where the localized action is desired. For the preparation of pro-TPA which is substantially free of TPA, a protease inhibitor, such as aprotinin or basic pancreatic trypsin inhibitor, is advantageously included during the purification procedure in order to inhibit traces of proteases which may be present and which may cause (partial) conversion of pro-TPA into TPA. The final purification is then effected by chromatography on a column containing a selective affinity reagent, such as DE-3, in the presence of an inhibitor which selectively binds only TPA and not pro-TPA, such as, for example, diisopropylfluorophosphate or nitrophenyl guanidinobenzoate. These reagents prevent TPA from adsorbing to the affinity column. Consequently, the bound TPA will pass through the DE-3 column whereas pro-TPA will adsorb to the column and can be eluted as described above.

Accordingly, it is a further object of the present invention to provide a process for the preparation of TPA, pro-TPA or mixtures thereof characterised in that serum-independent human cells or mutants thereof, capable of producing TPA, pro-TPA or mixtures thereof, such as Bowes II cells, are cultivated in a serum-free medium and the desired proteins are isolated from the harvest fluid and, if desired, a mixture of proteins obtained is separated or converted into the individual components. Specifically the present invention provides a process for the preparation of TPA which is free of pro-TPA, characterized in that pro-TPA present in a mixture obtained, is enzymatically converted into TPA. Especially, the present invention provides a process for the preparation of pro-TPA which is free of TPA, characterised in that a protease inhibitor is included during the isolation and the purification procedure and the final purification is effected in the presence of an inhibitor which selectively inhibits TPA.

Mixtures of TPA and pro-TPA as well as TPA and pro-TPA in substantially pure form, obtainable from serum independent human cells, especially from Bowes II cells, for example according to the above process, are new and are also objects of the present invention.

Pharmaceutical preparations

The new proteins, especially TPA and pro-TPA, obtainable from, for example, cultured Bowes II cells according to the present invention, exhibit valuable pharmacological properties. Thus, TPA and pro-TPA from Bowes II cells can be used in analogy to known plasminogen activators in humans for the prevention or treatment of thrombosis or other conditions where it is desired to produce local fibrinolytic or proteolytic activity via the mechanism of plasminogen activation, such as arteriosclerosis, myocardial and cerebral infarction, venous thrombosis, thromboembolism, post-surgical thrombosis, thrombophlebitis and diabetic vasculopathies.

The invention relates also to pharmaceutical preparations that contain a therapeutically effective amount of the active ingredient (especially TPA, pro-TPA or mixtures thereof) together with organic or inorganic, solid or liquid pharmaceutically acceptable carriers that are suitable for parenteral, i.e. intramuscular, subcutaneous or intraperitoneal, administration and that do not deleteriously interact with the active ingredients.

There are suitable especially infusion solutions, preferably aqueous solutions or suspensions, it being possible to prepare these before use, for example from lyophilized preparations that contain the active ingredient alone or together with a carrier, such as mannitol, lactose, glucose, albumin and the like. The pharmaceutical preparation may be sterilized and, if desired, mixed with adjuncts, for example preservatives, stabilisers, emulsifiers, solubilisers, buffers and/or salts for regulating the osmotic pressure. Sterilization can be achieved by sterile filtration through filters of small pore size (0.45 μm diameter or smaller) after which the preparation can be lyophilised, if desired. Antibiotics may also be added in order to assist in preserving sterility.

The pharmaceutical preparation according to the present invention are dispensed in unit dosage forms, for example ampoules, comprising 1 to 2000 mg of a pharmaceutically acceptable carrier per unit dosage and about 1 to 20 mg, preferably about 3 to 15 mg, of the active ingredient (TPA, pro-TPA or mixtures thereof) per unit dosage.

Depending upon the type of the disease and the age and the condition of the patient, the daily dose to be administered for the treatment of a patient weighing approximately 70 kg is in the range from 3 to 15 mg, preferably from 5 to 10 mg, per 24 hours.

The invention also concerns a method for producing a pharmaceutical preparation characterised in that a biologically active protein of the present invention is admixed with a pharmaceutically acceptable carrier.

The use of the new proteins for the prophylactic and therapeutic treatment of the human body is also an object of the present invention.

A further subject of the invention is the method of dissolving blood clots in humans wherein the fibrin of the blood clots is exposed to a TPA or pro-TPA or mixtures thereof obtained according to the invention.

The TPAs according to the present invention also exert their activity in vitro. Accordingly they can also be used as fibrinolytic agents together with plasminogen for example in washing and cleaning agents.

The invention concerns furthermore proteins whenever prepared according to the methods of the present invention.

The invention also extends to a serum-independent human cell line, e.g. a melanoma cell line, whenever obtained according to the process as set out herein.

The invention further extends to a biologically active compound, whenever obtained from a serum-independent human cell line, e.g. a melanoma cell line, as set out herein.

Further the invention extends to the use of the serum-independent human cell line as set out herein for the preparation of biologically active compounds under serum-free conditions.

The invention also extends to the use of Bowes II cultures for producing biologically active compounds under serum-free conditions.

The invention concerns especially the proteins and the processes for their preparation as described in the Examples.

The following Examples serve to illustrate the present invention but should not be construed as a limitation thereof.

| Experimental part | |
|---|---|
| Abbreviations used in the experimental part | |
| BPTI | basic pancreatic trypsin inhibitor |
| BSA | bovine serum albumin |
| DFP | diisopropylfluorophosphate |
| DMEM | Dulbecco's modified Eagle's medium |
| DTT | 1,4-dithiothreitol |
| EDTA | ethylenediaminetetraacetic acid |
| FCS | foetal calf serum |
| PBS | phosphate buffered saline (8 mM $Na_2HPO_4$; 1.5 mM $KH_2PO_4$; 0.14M NaCl; 2.7 mM KCl) |
| RPMI-1640 | Roswell Park Memorial Institute culture medium 1640 |
| SDS | sodium dodecyl sulphate |
| TCA | trichloroacetic acid |
| Tris | tris-(hydroxymethyl)-aminomethane |
| T—T (0.1) | 0.1M Tris.HCl pH 8.1 containing 0.1% Triton X-100 |

EXAMPLE 1

Establishment of the serum-independent cell line Bowes II a. Establishment of the Bowes II cell line with the aid of conditioned medium collected from Bowes I cells A human melanoma cell line [Bowes-RPMI 7272; described by D. C. Rijken and D. Collen, *J. Biol. Chem.* 256, 7035-7041 (1981)] was obtained from Dr. E. Reich, Rockefeller University, New York. The cell line is cultured in tissue culture flasks (150 cm², Costar) at 37° C. in a humid atmosphere of 95% air and 5% $CO_2$. The cells grow as adherent monolayers in Roswell Park Memorial Institute (RPMI) medium-1640 (Gibco) supplemented with sodium bicarbonate (2 g/l), antibiotics (300 μg/ml penicillin; 200 μg/ml streptomycin; 10 μg/ml tylocine), and 10% heat-inactivated (56° C.; 30 min.) foetal calf serum (FCS).

One tissue culture flask containing an adherent monolayer of cells is chosen. At confluence, the serum containing medium is removed and replaced with 50 ml of RPMI-1640 medium supplemented with antibiotics (see above). No other additives are included in this medium. The cells are kept at 37° C. in humid atmospheric air supplemented with 5% $CO_2$. The medium is changed at 24 hour intervals. Initially the cells appear healthy and remain adherent. After 12 days cells start to detach from the culture vessel and float free in the medium. After 14 days, the majority of cells have detached and a small fraction of viable cells still remains attached to the flask. The medium containing the detached cells is removed. The sparse adherent culture of melanoma cells which have been serum deprived for a prolonged period of time, is covered with 50 ml of new medium consisting of "conditioned medium" diluted with an equal volume of RPMI-1640. The "conditioned medium" is obtained as follows:

Serum containing medium is removed from confluent serum dependent melanoma cells Bowes-RPMI 7272 and is replaced with RPMI-1640 medium alone. 24 hours later, this medium is harvested, centrifuged at 2000 rpm for 5 min. and passed through a 0.45 $\mu m$ Millipore filter. The resulting solution is called "conditioned medium" and is immediately diluted with an equal volume of RPMI-1640.

"Conditioned medium" diluted with fresh RPMI-1640 is added to the culture at intervals of 4-5 days over a period of 3 months. After this time, the cell number has increased considerably and the serum-free culture no longer requires "conditioned medium". The culture is then fed with RPMI-1640 medium alone.

The serum-independent cells so obtained are cultured in tissue culture flasks (150 $cm^2$, Costar) and have to be seeded at a density of approximately $10^6$ cells/ml of medium to ensure survival. Cells are typically seeded at $5 \times 10^7$ cells/50 ml RPMI-1640/150 $cm^2$ flask. The cells grow very slowly in the serum-free medium and have a generation time of approximately 6 days (as compared to a generation time of approximately 24 hours for the serum-dependent cell line Bowes-RPMI 7272). At confluence, the cells are passaged by tapping the flask vigorously to dislodge adherent cells into the medium. Cells dislodged in this mechanical fashion are suspended in RPMI-1640 at a concentration of about $10^6$ cells/ml and used to reseed fresh tissue culture flasks. The cells not dislodged by the tapping procedure are supplied with fresh RPMI-1640 medium. In this manner, over a total period of 5 months, a culture of the serum-independent cell line Bowes II is established.

b. Establishment of the Bowes II cell line in the absence of conditioned medium collected from Bowes I cells 4 ml of a frozen stock of the serum-dependent melanoma cell line Bowes-RPMI 7272 (2.5·$10^6$ cells/ml in DMEM) containing 15% fetal calf serum and 10% DMSO are thawed and added to 15 ml serum-free, prewarmed DMEM in a 75 $cm^2$ tissue culture flask. The cells are incubated overnight at 37° C. in humid atmospheric air supplemented with 5% $CO_2$. After this period the entire medium including nonadhering cells is removed and replaced by 15 ml serum-free DMEM. Incubation is continued until cells appear granulated under the microscope (24-72 hours) at which point 50% of the medium is removed and replaced with fresh serum-free DMEM. This procedure is repeated every two to three days as necessary (microscopic appearance of cells, pH-change of the medium) gradually increasing the total volume of the medium to 30 ml. When 60-70% confluency is reached (about 3 weeks) the cells are passaged into two new flasks of equal size using 0.02% EDTA to detach the cells from the surface of the culture dish. At first passaging serum-free DMEM is supplemented to 40% with medium removed from the culture prior to EDTA-treatment. At this point, the serum-free line is established and the cells will continue to divide in the absence of conditioned medium if maintained at sufficiently high cell density, i.e. at 30% confluency at least.

EXAMPLE 2

Cultivation of Bowes II cells in submerged culture

Bowes II cells grown to confluence in tissue culture flasks in serum-free medium RPMI-1640 are dislodged by tapping the flasks vigorously by hand, pooled to give 0.6 l suspension containing $2 \times 10^5$ cells/ml and transferred to a 3 l steam sterilised glass vessel. The cell suspension is slowly agitated with a mechanical stirrer (40 r.p.m.). The temperature is controlled at 37°±0.1° C. and the culture is provided with oxygen by surface aeration with air containing 5% $CO_2$ at a rate of 0.2 l/min. The pH is prevented from dropping below 6.9 by reverting to pure air. During the initial adaption period of about one week fresh serum-free medium is added to prevent depletion of glucose. The final culture volume is 1 liter When the cell density has reached $3-4 \times 10^5$ cells/ml, periodic withdrawal of culture liquid is started. Every 2-4 days, agitation is interrupted for 3 hours to allow most of the viable cells to sediment and the upper 50% of the spent medium is withdrawn and replaced by fresh serum-free medium. The harvest fluids are centrifuged at 2000 rpm (~300 g) for 5 min. to remove whole cells and cellular debris. The solutions are stabilised with Triton X-100 ® to a final concentration of 0.1% and acidified with acetic acid to pH 5.5-6.0 prior to storage at −20° C.

EXAMPLE 3

Cultivation of Bowes II cells in tissue culture flasks and collection of harvest fluids The serum-independent cell line Bowes II is inocculated at $5 \times 10^7$ cells/150 $cm^2$ tissue culture flask (Costar) in 50 ml RPMI-1640 supplemented with antibiotics (cf. Example 1) at 37° C. in a humid atmosphere of 95% air and 5% $CO_2$. When the cells have become adherent, the medium is collected from the cells and replaced by fresh RPMI-1640 supplemented with antibiotics. The taking of serum-free harvest fluids is repeated at 24 hour intervals until confluence of the monolayer necessitates passaging. Confluence is reached after approximately 5 weeks. Passaging is performed as described in Example 1. The harvest fluid is processed as described in Example 2.

EXAMPLE 4

Determination of content of TPA and pro-TPA in harvest fluids

The harvest fluids containing TPA and pro-TPA are treated with $^3$H-DFP (diisopropylfluorophosphate) of known specific activity. After incubation the labelled enzymes are recovered and freed from unreacted radioactive DFP by precipitation and washing with trichloroacetic acid using the methods recommended in the literature for serine proteases [J. A. Cohen et al., *Methods in Enzymology*, Vol. XI, p. 868 (1967)]. This active site titration of the activator establishes that the harvest fluids collected from serum-independent Bowes II cells contain approximately 10-20 nmol of total TPA per liter.

The release of total TPA (TPA and pro-TPA) by Bowes I and Bowes II cells over 4 consecutive days can be determined as follows:

Harvest fluids from Bowes I melanoma cells grown in 75 cm$^2$ tissue culture flasks ($1.3 \times 10^5$ cells/cm$^2$; 20 ml/flask) or Bowes II cells grown in 150 cm$^2$ flasks ($4 \times 10^5$ cells/cm$^2$; 50 ml/flask) are taken every 24 hr over 4 days. Plasminogen activator activity is measured in the $^{125}$I-fibrin assay (see below). TPA release stays constant over the 4 day period in the case of Bowes II cells, whereas in the case of Bowes I melanoma cells, TPA activity increases slightly over the first 3 days, but then decreases on the 4th day. By this time most of the cells have detached from the surface, and RPMI supplemented with 10% FCS has to be added to restore adherence. (cf. Table 1).

In the $^{125}$I-fibrin assay [E. L. Wilson and E. Dowdle, *Int. J. Cancer* 22, 390-399 (1978)] a solid-phase substrate is provided by radioactive $^{125}$I-fibrinogen/fibrin deposited as a thin layer on the bottom inside surface of plastic tissue culture wells. Samples of harvest fluids to be assayed are added to the wells and TPA activity is measured as plasminogen-dependent solubilization of radioactivity as a function of time. Since the $^{125}$I-fibrin assay measures both TPA and pro-TPA activity the results given for TPA activity in Table 1 refer to total enzyme.

TABLE 1

Total TPA release by serum-dependent Bowes I melanoma cells and serum-independent Bowes II cells in tissue culture flasks expressed in international urokinase (UK) units.

| Cell type | Time (days) | Total TPA (UK μ) |
|---|---|---|
| Bowes melanoma I | 1 | 1154 |
|  | 2 | 1254 |
|  | 3 | 1380 |
|  | 4 | 976 |
| Bowes II | 1 | 3560 |
|  | 2 | 3660 |
|  | 3 | 3950 |
|  | 4 | 3850 |

In addition, the culture fluids of both serum-dependent Bowes melanoma cells and serum-independent Bowes II cells are assayed for individual content of TPA and pro-TPA:

Bowes I melanoma cells are plated at $5 \times 10^5$ cells per replicate 35 mm dish in 2 ml RPMI containing 10% FCS. After 24 hr the medium is replaced with serum free RPMI and 24 hr harvest fluids are collected for 3 consecutive days. At the end of each 24 hr period the cell number per plate is counted.

Bowes II cells are plated at $3 \times 10^6$ cells per 35 mm dish in 2 ml RPMI.

Plasminogen activator activity is determined using the fluorometric assay with Cbz-Gly-Gly-Arg-AMC as substrate. The direct amidolytic action of TPA is measured fluorometrically by following the rate of increase in fluorescence at 455 nm that results from the amidolytic release of aminomethyl coumarin (AMC) from the fluorogenic substrate [cf. M. Zimmerman et al., *Proc. Natl. Acad. Sci.* USA 75, 750-753 (1978)]. 1 FU represents that amount of enzyme which hydrolyses 10 pmol of substrate in one minute in the amidolytic assay. The results are depicted in Table 2.

TABLE 2

Release of TPA and pro-TPA by serum-dependent Bowes I melanoma cells and serum-independent Bowes II cells.

| | | | Plasminogen activator release (FU/10$^6$ cells/24 hr) | | |
|---|---|---|---|---|---|
| Cell type | Days in culture | Cell density (cells $\times 10^5 \times$ cm$^{-2}$) | Total activity$^{(a)}$ | TPA (%) | pro-TPA (%)$^{(b)}$ |
| Bowes melanoma I | 1 | 1.04 | 46.62 | 87.5 | 12.4 |
|  | 2 | 1.27 | 51.96 | 92.1 | 7.9 |
|  | 3 | 1.43 | 64.86 | 83.9 | 16.1 |
| Bowes II | 1 | 3.88 | 26.06 | 12.7 | 87.3 |
|  | 2 | 3.88 | 25.10 | 12.4 | 87.5 |
|  | 3 | 4.01 | 24.40 | 10.9 | 88.9 |

$^{(a)}$Total TPA activity is measured after incubation of 295 μl harvest fluid with 5 μl plasmin (0.1 mg/ml) for 60 min. at room temperature. Plasmin is inhibited by Trasylol ® for the assay.
$^{(b)}$The amount of proactivator (pro-TPA) is estimated by substracting the activity measured without plasmin activation from the total activity.

As can be seen from Table 2, approximately 10% of the TPA secreted by the serum-independent Bowes II cells is in the form of the active enzyme and approximately 90% is in the form of pro-enzyme (pro-TPA). In contrast, medium collected from the serum-dependent Bowes I melanoma cells contains 90% TPA and approximately 10% pro-TPA.

EXAMPLE 5

Recovery and purification of TPA and pro-TPA a. Preparation of a DE-3 sepharose ® column 26 mg of purified DE-3 inhibitor from *Erythrina latissima* [F. J. Joubert et al., *Hoppe-Seyler's Zeitschr. Physiol. Chem.* 302, 531-538 (1981)] are coupled to 5 ml of cyanogen bromide activated Sepharose 4b ® (Pharmacia) according to the manufacturer's instructions. The matrix is equilibrated with phosphate buffered saline ("PBS") pH 7.4 containing 0.4M NaCl, 0.1% Triton X-100 ® and 0.02% sodium azide. The matrix is then packed into a 5 ml column.

b. Chromatographical purification of TPA and pro-TPA containing harvest fluids on DE-3 Sepharose 4b ®

Two liters of harvest fluid obtained from serum-independent Bowes II cells (see Example 3) is made 0.4M with respect to NaCl and 0.1% with respect to Triton X-100 ® and filtered through a 0.45 μm membrane (Millipore). The harvest fluid is then applied to the DE-3 Sepharose ® column (see above) at a flow rate of 45 ml/hr at room temperature and the effluent is discarded. After the total volume of harvest fluid has passed through, the column is washed with approximately 50 ml of PBS containing 0.4M NaCl and 0.1% Triton X-100 ®. Adsorbed proteins are then eluted using PBS containing 1.6M KSCN, 0.4M NaCl and 0.1% Triton X-100 ®, and 2 ml fractions are collected at 4° C. The protein content of each fraction is determined by measuring the UV absorbance at 280 nm. The adsorbed protein is found to be eluted as a sharp peak. Fractions containing the highest UV absorbance and highest fibrinolytic activity as determined in the $^{125}$I-fibrin assay are pooled to give 8 ml of solution which is stored at $-20°$ C. This represents approximately 70–80% of the total activity applied to the column. Fractions containing lower activity are pooled separately. The total recovery of activity in both pools usually amounts to 90–100%.

A sample is taken from the pool. The protein is precipitated by adding trichloroacetic acid to a final concentration of 10%, and is subjected to SDS polyacrylamide gel electrophoresis. The electrophoretogram shows a single band of protein with an approximate molecular weight of 73,000 daltons as determined according to the method of Weber and Osborne [J. Biol. Chem. 244, 4406–4412 (1969)] using co-electrophoresed marker proteins of known molecular weight.

The TPA and pro-TPA content of the combined pool is determined using the fluorometric assay with Cbz-Gly-Gly-Arg-AMC as substrate (cf. Example 4). Total TPA activity is measured after incubation with plasmin which is inhibited by Trasylol for the assay. The amount of pro-TPA is estimated by subtracting the activity measured without plasmin activation from the total activity. It can be established that purification of plasminogen activator from the medium of Bowes II cells yields a mixture of TPA and pro-TPA in about equal proportions. Thus, pro-TPA is partly converted to the active enzyme during the isolation procedure as in the unprocessed harvest fluids collected from Bowes II cells the proportion of TPA is 10% and pro-TPA is 90% (cf. Example 4. Table 2).

Treatment of the harvest fluids from the serum-independent Bowes II cell line with low concentrations of foetal calf serum (0.01%) results in conversion of pro-TPA to TPA. This is presumably due to the presence of plasmin in FCS.

c. Chromatographical purification of TPA and pro-TPA containing harvest fluids on DE-3 sepharose 4b in the presence of a proteinase inhibitor Chromatography of harvest fluids obtained from serum-independent Bowes II cells is carried out in a similar manner as described in Example 5b, except that basic pancreatic trypsin inhibitor (BPTI) at 0.1 KIU/ml is included in the procedure. Using the fluorometric assay with Cbz-Gly-Gly-Arg-AMC as substrate (see above), the TPA and pro-TPA contents of the purified solution are determined, 90% of the TPA is in the pro-enzyme form and 10% is in the active form. Thus, the conversion of pro-TPA to TPA during the purification procedure is inhibited by BPTI.

EXAMPLE 6

Evidence for the presence of one chain pro-TPA in purified TPA preparations

Harvest fluids obtained from the serum-independent cell line Bowes II are purified by affinity chromatography on DE-3 Sepharose ® as described in Example 5c. In the resulting purified solution approximately 90% of the TPA is in the pro-enzyme form and approximately 10% is in the active enzyme form as judged by the amidolytic assay before and after plasmin treatment. The solution is dialysed into T-T (0.1). Samples of this solution are mixed with equal volumes of PBS or PBS containing 5 µg/ml of plasmin. After incubation for 16 hr at 20° C., SDS is added to a final concentration of 0.1% and the proteins are precipitated with 6% TCA. The precipitates from 200 µl samples of original enzyme solution are washed in acetone and redissolved in 20 µl of 0.06M Tris-HCl pH 6.8 containing 1% SDS and 10% glycerol. Where necessary, these samples are reduced at this stage by the addition of 2 µl of 1M DTT and incubated at 37° C. for 30 min. All samples are then boiled for 1 min, and 20 µl of each is electrophoresed in a 5–15% polyacrylamide slab gel containing 0.1% SDS. After electrophoresis the gel is stained with Coomassie brilliant blue ® and destained as usual. The electrophoretic tracks contain (a) molecular weight markers, (b) untreated and nonreduced TPA solution, (c) untreated and reduced TPA solution, and (d) plasmin-treated and reduced TPA solution.

Track (b) shows only one protein band with a molecular weight of approximately 73000. Under reducing conditions (track c) most of the TPA also migrates in the 73000 dalton region. However, additional weak bands can be observed in the 35000 dalton region. Plasmin treatment and reduction with DTT converts the 73000 dalton protein into two subunits with apparent molecular weights of 35000 daltons and 38000 daltons, respectively. These experiments demonstrate that the single chain pro-TPA having a molecular weight of 73000 daltons is converted by plasmin treatment to the S-S-linked two chain form (TPA). TPA is then cleaved under reducing conditions to give the two subunits.

EXAMPLE 7

Determination of the enzymatic activity of pro-TPA

Samples (500 µl) of a TPA preparation containing approximately 20 FU/ml of total activator (TPA and pro-TPA) in T-T (0.1) are incubated in the presence (a and b) or in the absence (c and d) of 5 mM DFP for 60 min at 20° C. Free DFP is removed according to the method of H. S. Penefsky [J. Biol. Chem. 252, 2891–2899 (1977)] by centrifugation of 100 µl samples of the reaction mixtures through 1 ml columns containing Sephadex G25 ® fine equilibrated with T-T (0.1). Volumes of 3 µl of 0.5 mg/ml plasmin (b and d) or 3 µl of PBS (a and c) are added to these samples and they are incubated for 30 min at 20° C. Fifty microliters of each sample is then removed from the solution and added to 10 µl BPTI (1000 KIU/ml) to inhibit plasmin activity. The amidolytic activity in each sample is determined using the fluorometric assay. The results are depicted in Table 3.

TABLE 3

| Activation of DFP-resistant pro-TPA with plasmin. | | |
|---|---|---|
| Treatment | | |
| DFP | Plasmin | Activity (FU/ml) |
| (a) + | − | 0.00 |
| (b) + | + | 8.23 |
| (c) − | − | 6.25 |
| (d) − | + | 17.48 |

The sample has a total TPA content of 17.48 FU/ml (d) of which 6.25 FU/ml is present in active enzyme form (c). The active enzyme is inhibited to undetectable levels by treatment with DFP (a). After treatment with DFP active enzyme can be generated by incubation with plasmin (b), showing that pro-TPA is resistant to DFP treatment and lacks measurable enzyme activity.

EXAMPLE 8

Separation of pro-TPA from TPA

The solution of TPA (10%) and pro-TPA (90%) obtained as described in Example 5c is adjusted to pH 8.0 with 0.1M Tris·HCl containing 0.1% Triton X-100 ® and rendered 1 mM with respect to DFP. After incubation at 37° C. for 4 hours, the mixture is passed through a 5 ml DE-3 Sepharose column (cf. Example 5a). The effluent containing the irreversibly inhibited TPA is discarded. The column is washed with 6 column volumes of PBS containing 0.4M NaCl and 0.1% Triton X-100 ® and subsequently eluted with PBS containing 1.6M KSCN, 0.4M NaCl and 0.1% Triton X-100 ® as described in Example 5b. Fractions showing the highest UV absorbance are pooled. The pool contains pro-TPA in substantially pure form as no amidolytic activity is detectable in the fluorometric assay using Cbz-Gly-Gly-Arg-AMC as substrate. The amidolytic as well as the fibrinolytic activity can be re-established by treatment with plasmin which converts pro-TPA into the active enzyme.

EXAMPLE 9

The binding of TPA and pro-TPA to insolubilized fibrin

Five samples containing TPA and pro-TPA in different proportions are obtained as described in Example 5c or by partially converting pro-TPA to TPA in such a solution. Their contents of active TPA and pro-TPA are determined from the results of fluorometric assays before and after plasmin treatment as described in Example 4. These samples are then diluted in T-T (0.1) so that 0.2 ml would, in the presence of 2 µg of plasminogen, release approximately 30 to 50% of the $^{125}$I-fibrin coated on the bottom of Linbro wells in 1 hr.

Aliquots (0.2 ml) of the samples are then added in quadruplicate to Linbro wells coated with $^{125}$I-fibrin (30 µg; 100 000 cpm). After incubation for 1 hr at 0° C. two wells of each quadruplicate set are washed three times with T-T (0.1) to remove unbound TPA proteins.

Bound activity is measured as the amount of $^{125}$I-fibrin solubilized in 1 hr after the addition of 0.3 ml of Tris·HCl pH 8.1 containing 2 µg of plasminogen and 80 µg of BSA. Total TPA activity added to the wells is measured as the amount of $^{125}$I-fibrin solubilized in 1 hr after the addition of 2 µg of plasminogen and 80 µg of BSA (0.3 ml of the same buffer) to wells that have not been washed.

The results are depicted in Table 4.

TABLE 4

The binding of pro-TPA to insolubilized fibrin

| | | fibrinolytic activity (% $^{125}$I-fibrin solubilized in 60 min) | | |
|---|---|---|---|---|
| Sample | % pro-TPA | Total activity | Activity after wash | % bound |
| 1 | 88.7 | 29.83 | 29.48 | 98.8 |
| 2 | 34.0 | 45.90 | 37.52 | 81.7 |
| 3 | 64.0 | 56.56 | 41.53 | 73.4 |
| 4 | 87.0 | 48.88 | 48.76 | 99.8 |
| 5 | 88.0 | 53.85 | 52.49 | 97.5 |

Table 4 indicates that a larger percentage of total TPA enzyme is bound to insolubilized fibrin when the TPA preparation is in the pro-activator form.

EXAMPLE 10

Pharmaceutical preparation for parenteral administration

A TPA and/or pro-TPA containing solution obtained as described in Example 5b, 5c or 8, is dialysed against 0.3 molar sodium chloride containing 0.01% Tween 80 ® and stored at −80° C. Prior to administration the concentration is adjusted to 75 µg/ml of total TPA (i.e. TPA or pro-TPA or TPA plus pro-TPA) and 0.3M NaCl. The solution is sterilised by filtration through a 0.22 µm membrane filter.

This procedure is suitable for the preparation of solutions of TPA, pro-TPA or TPA plus pro-TPA for parenteral, such as intravenous, administration.

EXAMPLE 11

Selection of a mutant of the serum-independent cell line Bowes II capable of producing increased levels of TPA 5% foetal calf serum is added to a Petri dish culture of the serum-independent Bowes II cell line in order to increase the growth rate of the cells and to ensure that more cells will be in the s phase at one particular time. When the cells are rapidly dividing and in the exponential growth phase and when they are approximately 70% confluent, 0.1 mM of N-methyl-N-nitro-N'-nitrosoguanidine (MNNG) is added to the culture. This concentration causes the death of about 70 to 80% of the cells. After 36 hours the remaining viable cells are removed from the Petri dish by trypsinization. The cells are reseeded at a density of $1.10^5$ cells/60 mm Petri dish. Two weeks later, colonies of cells are observed at the bottom of the dish, each colony representing the progeny of a simple cell that survived the mutagenesis. These colonies are then covered with 1 ml of an overlay solution which contains 50 µl of plasminogen (1 mg/ml),
300 µl of 8% casein in isotonic saline,
600 µl of 2.5% agar in isotonic saline and
800 µl of RPMI-1640 medium.

Areas of lysis develop around the clones producing TPA and the largest areas of lysis are seen around the clones producing the most TPA. The mutant clone producing the highest level of TPA is isolated and expanded on a Petri dish.

I claim:

1. A process for producing proteins, comprising culturing, in a culture medium deprived of serum and exogenous macromolecular growth factors, cells of a human melanoma cell line, derived from a serum-dependent human melanoma cell line, which cells are capable of reproducibly and indefinitely propagating in culture in a medium deprived of serum and exogenous macromolecular growth factors and which produce said proteins, harvesting fluid from said culture, and isolating proteins from said harvested fluid.

2. A human melanoma cell line, derived from a serum-dependent human melanoma cell line, capable of reproducibly and indefinitely propagating in culture in a medium deprived of serum and exogenous macromolecular growth factor.

3. A process for the production of a human melanoma cell line capable of reproducibly and indefinitely propagating in culture in the absence of serum and in the absence of exogenous macromolecular growth factors, comprising the steps of:

(a) establishing a culture of a serum-dependent human melanoma cell line in a culture medium containing serum;

(b) removing the culture medium containing serum from said culture and replacing it with a culture medium deprived of serum and deprived of exogenous macromolecular growth factors;

(c) feeding the adherent and any non-adherent cells with culture medium deprived of serum and deprived of exogenous macromolecular growth factors; and (d) culturing the cells until they propagate reproducibly and indefinitely in culture medium deprived of serum and deprived of exogenous macromolecular growth factors, thereby establishing a human melanoma cell line which is capable of reproducibly and indefinitely propagating in medium deprived of serum and deprived of exogenous macromolecular growth factors.

4. The process according to claim 3 comprising the further step of subjecting the established human melanoma cell line of step (d) to a treatment selected from group consisting of treatment with a mutagen, exposure to X-rays, and exposure to ultraviolet radiation, to produce an established mutant cell line thereof capable of reproducibly and indefinitely propagating in medium deprived of serum and deprived of exogenous macromolecular growth factor.

5. A process for the production of a human melanoma cell line capable of reproducibly and indefinitely propagating in culture in the absence of serum and in the absence of exogenous macromolecular growth factors, comprising the steps of:

(a) establishing a culture of a serum-dependent human melanoma cell line in a culture medium containing serum;

(b) removing the culture medium containing serum from said culture and replacing it with a culture medium deprived of serum and deprived of exogenous macromolecular growth factors;

(c) periodically removing from said culture essentially the entire medium and any non-adherent cells, separating the non-adherent cells from said removed medium, and adding back to the remaining adherent cells in culture said non-adherent cells and fresh medium deprived of serum and exogenous macromolecular growth factors; and (d) repeating the removal, separating and addition back procedures of step (c) until the adherent cells in culture propagate reproducibly and indefinitely in fresh culture medium deprived of serum and deprived of exogenous macromolecular growth factors, thereby establishing a human melanoma cell line capable of reproducibly and indefinitely propagating in medium deprived of serum and exogenous macromolecular growth factors.

6. A process for the production of a human melanoma cell line capable of reproducibly and indefinitely propagating in culture in the absence of serum and in the absence of exogenous macromolecular growth factors, comprising the steps of:

(a) establishing a culture of a serum-dependent human melanoma cell line in a culture medium containing serum;

(b) removing said culture medium containing serum from said culture and replacing it with a culture medium deprived of serum and deprived of exogenous macromolecular growth factors;

(c) thereafter periodically removing at least a portion of the medium from said culture and replacing it with fresh medium deprived of serum and exogenous macromolecular growth factors;

(d) repeating the removal and replacement of step (c) until a confluency of adherent cells in culture of at least 30% is obtained; and (e) dislodging the adherent cells and culturing them in the presence of medium comprised of a mixture of a portion of the medium removed from the culture prior to said dislodging and fresh medium deprived of serum and deprived of exogenous macromolecular growth factors to produce an established human melanoma cell line capable of reproducibly and idefinitely propagating in medium deprived of serum and exogenous macromolecular growth factors.

7. The process according to claim 6 wherein said dislodging of adherent cells is performed after a confluency of at least about 60% is obtained.

8. A process for producing a human melanoma cell line capable of reproducibly and indefinitely propagating in culture in the absence of serum and in the absence of exogenous macromolecular growth factors, comprising the steps of:

(a) establishing a culture of a serum-dependent human melanoma cell line in a culture medium containing serum;

(b) removing said culture medium containing serum from said culture and replacing it with culture medium deprived of serum and exogenous macromolecular growth factors;

(c) periodically adding to the culture a medium deprived of serum and exogenous macromolecular growth factors and comprised of a medium harvested from a companion cell culture of said serum-dependent cells after replacement therein of medium containing serum with medium deprived of serum and exogenous macromolecular growth factor; and (d) continuing said periodic addition of step (c) until there is obtained an established human melanoma cell line capable of reproducibly and indefinitely propagating in culture in a medium deprived of serum and exogenous macromolecular growth factors.

* * * * *